United States Patent [19]

Ramasamy et al.

[11] Patent Number: 5,907,036

[45] Date of Patent: May 25, 1999

[54] PROCEDURES FOR OBTAINING RIBO-C-NUCLEOSIDES

[75] Inventors: Kandasamy Ramasamy, Laguna Hills, Calif.; Arthur F Lewis, The Woodlands, Tex.; Roland K Robins, deceased, late of Provo, Utah, by Lessa R Robins, legal representative; Natarajan Raju, Kendall Park, N.J.; Ramesh Bharadwaj, Norwalk, Calif.; Vjera Pejanovic, Belgrade, Yugoslavia

[73] Assignee: ICN Pharmaceuticals, Inc., Costa Mesa, Calif.

[21] Appl. No.: 08/603,106

[22] Filed: Feb. 20, 1996

[30] Foreign Application Priority Data

Feb. 17, 1995 [YU] Yugoslavia ............... 96/95
Mar. 7, 1995 [YU] Yugoslavia ............... 151/95

[51] Int. Cl.$^6$ ............... C07H 1/00; C07H 7/06
[52] U.S. Cl. .................. 536/55.3; 536/29.2
[58] Field of Search ........................ 536/55.3, 29.2

[56] References Cited

U.S. PATENT DOCUMENTS 4,451,648  5/1984  Parsons et al. ............... 536/55.3

*Primary Examiner*—Gary L. Kunz
*Attorney, Agent, or Firm*—Robert D. Fish; Crockett & Fish

[57] ABSTRACT

Novel procedures for obtaining ribo-C-nucleosides, including especially 2-β-D-ribofuranosylthiazole-4-carboxylamide (tiazofirin) and 2-β-D-ribofuranosylselenazole-4-carboxylamide (sylenazofurin) and synthesis intermediates thereof. The novel procedures involve introducing a cyano group at the 1' position of a ribose, directly or indirectly converting the cyano group to $HN=C-OR_1$ or thicarboxylamide wherein $R_1$ is a lower alkyl, forming the group which substituted for the cyano group into a heterocyclic ring containing an ester, and converting the ester into an amide.

11 Claims, No Drawings

PROCEDURES FOR OBTAINING RIBO-C-NUCLEOSIDES

TECHNICAL FIELD

The invention described herein relates to the field of organic chemistry technology, more specifically to the field of manufacturing of synthetic drugs of the C-nucleosides group.

SUMMARY OF THE INVENTION

Described and claimed herein are novel procedures for obtaining ribo-C-nucleosides, primarily 2-β-D-ribofuranosylthiazole-4-carboxamide (tiazofurin), and 2-β-D-ribofuranosylselenazole-4-carboxamide (selenazofurin), as well as intermediates in the synthesis. Depending on the embodiments, the procedure may be shortened by at least one step over the prior art. In addition duration of each step may be significantly decreased (formation of intermediates) and higher yield may be achieved, which altogether results in a much more economical procedure.

PRIOR ART

2-β-D-ribofuranosylthiazole-4carboxamide (tiazofurin), an antiviral and antitumor agent already known in the literature, was synthesized in 1976 concurrently by M. Fuertes et al. (J.Org.Chem. 1976, 41(26), 4074) and P. C. Srivastava et al. (J.Med.Chem. 1977, 20, 256), with a yield of 6% and 26% respectively. According to the above authors, the synthesis takes place in several steps. From the parent compound 1-O-acetyl-2,3,5-tri-O-benzoyl-β-D-ribofuranose, with the aid of gaseous hydrogen bromide, 1-bromo-2,3,5-tri-O-benzoyl-β-D-ribofuranose is synthesized, which with mercury cyanide produces 2,3-anhydro-3,4,6-tri-O-benzoyl-β-D-allononitrile (cyano sugar), which, again, with hydrogen sulfide, produces thioamide. By a classic Hantzsch's synthesis of thioamide and ethyl-α-bromopyruvate, ethyl thiazole is obtained, which is subjected concurrently to debenzoylation and ammonolysis. The principal disadvantages of the cyano sugar synthesis, with the cyano sugar being synthesized in two steps, according to the original synthesis (M. Bobek and J. Farkas, Collect. Czech.Chem.Commun. 1969, 34, 247), include: a great surplus of dry gaseous hydrogen bromide, unstableness of bromo-sugar which, for this reason, cannot be stored, but reacts immediately with a highly toxic mercury cyanide, in a highly flammable nitramethane. Thioamide, the next intermediate, was synthesized by P. C. Srivastava et al. by means of liquid hydrogen sulfide, while M. Fuertes et al. used gaseous hydrogen sulfide, achieving a yield of only 20%, which resulted in an exceptionally low total yield. In the step of thiazolic ring formation, a high percentage of the undesired α-anomer is also produced. The methanolysis of benzoyl ester and formation of the desirable amide take place in one step, with the release of benzamide, thus requiring chromatographic purification.

2-β-D-ribofuranosylselenazole-4-carboxamide (selenazofurin), with stated significant antitumor activity in animals and a broad spectrum of antiviral activities in cell cultures, was synthesized by C. Srivastava and R. K. Robins (J.Med.Chem. 1983, 26, 445); R. K. Robins and C. Srivastava (U.S. Pat. No. 4,531,001; July 1985, U.S. Pat. No. 4,594,414; June 1986, U.S. Pat. No. 4,594,416; June 1986), in a yield of 22%. The mentioned authors also started from 2,3-anhydro-3,4,6-tri-O-benzoyl-β-D-allononitrile, which, when treated with liquid hydrogen selenide for 20 hours at room temperature, produces selenium amide, which then reacts with ethyl-α-bromopyruvate in acetonitrile. In this reaction, a mixture of desired ethyl 2(2,3,5-tri-O-benzoyl-β-D-ribofuranosyl)-4-selenazolcarboxylate and inactive α-anomer is obtained, thus requiring column chromatographic purification, followed by ammonolysis of active β-anomer until selenazofurin is obtained.

Main disadvantages of the aforementioned methods include the use of liquid hydrogen sulfide and selenide, respectively, this requiring the application of an autoclave, long duration of the reaction of carboxamide formation, isolation of unstable selenium amide, use of acetonitrile as a solvent, the production of α-anomer, which all results in a low total yield.

Parsons J. L. et al. (U.S. Pat. No. 4,451,684) have modified the above procedure for obtaining tiazofurin, through eliminating some disadvantages, by using methylene chloride instead of nitromethane and gaseous hydrogen sulfide instead of the liquid one, which resulted in a decrease formation of α-anomers. The disadvantages of their procedure still include the two-step synthesis of cyano sugar with gaseous hydrogen bromide, the use of petrol ether in purification of cyano sugar, the long reaction time for the formation of thiazolic ring (86 hours), thioamide (21 hours) and tiazofurin (72 hours), and the use of chromatography to purify ethyl ester of thiazole and deblocked methyl ester, which increases procedure costs and reduces yield—a total yield being only 16%.

P. D. Cook and D. J. McNamara (J. Heterocyclic Chem. 1986, 23, 155) have, by analogy to tiazofurin synthesis (J. L. Parsons et al., U.S. Pat. No. 4,451,648 May 1984), optimized the selenazofurin synthesis by introducing gaseous hydrogen selenide instead of the liquid one, in equimolar proportion, which resulted in the decrease of α-anomer formation. In this way, a technically more feasible and safer synthesis was obtained, with a yield of approximately 41 %.

W. J. Hennen et al. (J.Org.Chem. 1985, 50, 1741) have published a somewhat different method for the synthesis of ribo-C-nucleosides, with a yield of approximately 19% for tiazofurin and approximately 13% for selenazofurin. According to their method, cyano sugar is, with sodium methoxide, converted into iminoester, which with hydrogen sulfide yields thio- and selenoester, respectively. Condensation with ethyl-2-amino-2-cyanoacetate produces thiazole, which transforms into tiazofurin or selenazofurin in two steps—reduction deamination with $HNO_2$—$H_3PO_2$ and ammonolysis. The main disadvantages of this procedure are a low yield and chromatographic purification in severed steps.

2,3-anhydro-3,4,6-tri-O-benzoyl-β-D-allononitrile (cyano sugar) is a common intermediary for all the aforementioned syntheses and in view of the fact that it is not commercially available, the cost-effectiveness of tiazofurin and selenazofurin syntheses depends considerably on the method of synthesis and the yield of cyano sugar. F. G. de las Heras and P. Fenandez-Resa (J.Chem.Soc.Perkin Trans 1, 1982, 903) have published a one-step synthesis of cyano sugar with trimethylsilyl cyanide, with stannic(IV)chloride as a catalyst, however, with much surplus of a very costly trimethylsilyl cyanide (the ratio to cyano sugar expressed in moles was 1:4) in acetonitrile and with the use of chromatographic purification. P. D. Cook and D. J. McNamara (J. Heterocyclic Chem. 1986, 23, 155) have used methylene chloride instead of acetonitrile, with the proportion of 1-O-acetyl-2,3,5-tri-O-benzoyl-β-D-ribofuranose to trimethylsilyl cyanide being 1:2, and to stannic(IV)chloride being 1:1. The reaction takes place at room temperature, and for this reason side products are formed, which make purification difficult.

Because of the interesting features of C-nucleosides, two more papers have been published in the '90-ties on the synthesis of tiazofurin and of ribo-C-nucleosides in general. R. M. Bimwala and P. Vogel (Helv.Chim.Acta 1989, 72, 1825) published a paper on the total synthesis of tiazofurin and ribo-C-nucleosides precursor, which, starting from an optically pure 7-oxabicyclo [2.2.1]hept-5-en-2-yl ester (1.S) of camphanoyl produces tiazofurin in nine steps, with a yield of 25%. In view of a large number of steps and a low yield, this synthesis is of no significant practical importance.

D. C. Humber et al. (J.Chem.Soc.Perkin Trans.1, 1990, 283) worked on synthesis of tiazofurin and N-substituted tiazofurins, starting from benzyl (2',3',5'-tri-O-benzoyl-β-D-ribofuranosyl)penicillinate. The yield in this synthesis is approximately 12%.

DESCRIPTION OF THE TECHNICAL PROBLEM SOLUTION

Described herein are novel procedures for obtaining the ribo-C-nucleosides, which provides primarily 2-β-D-ribofuranosylthiazole-4-carboxamide (tiazofurin), 2-β-D-ribofuranosylselenazole-4-carboxamide (selenazofurin) and ribosethiocarboxamide; apart from this, the procedure of the invention provides a new method of synthesis of ethyl-2-β-D-ribofuranosylselenazole-4-carboxylate, an intermediate in selenazofurin synthesis.

The advantages of the procedure of the invention include a synthesis procedure shortened by one step, a substantially decreased duration of certain steps (forming of intermediates) and a significantly higher yield, all this resulting in a much more economical procedure.

The procedure of the invention is a multi-step one, wherein in step (a) 2,3-anhydro-3,4,6-tri-O-benzoyl-β-D-allononitrile (cyano sugar) is obtained from 1-O-acetyl-2,3,5-tri-O-benzoyl-β-D-ribofuranose, to be converted with sodium methoxide in step (b) into methyl-2,5-anhydro-D-allonimidate, which, with gaseous reagent produces an amide in step (c), whereas, depending on the type of desired final product, hydrogen sulfide (producing thioamide) and/or hydrogen selenide (producing selenium amide) are used as gaseous reagents. In the next step (d), by condensation of thio- or selenoamide, previously unisolated, with ethyl-α-bromopyruvate—carboxylate is obtained, which is then, in step (e), converted by ammonolysis to tiazofurin and selenazofurin, respectively. The procedure can be represented by the following scheme:

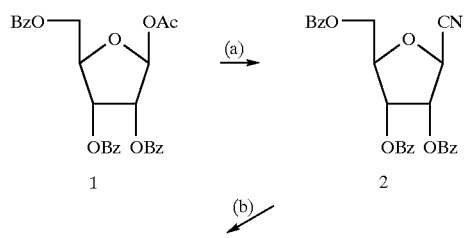

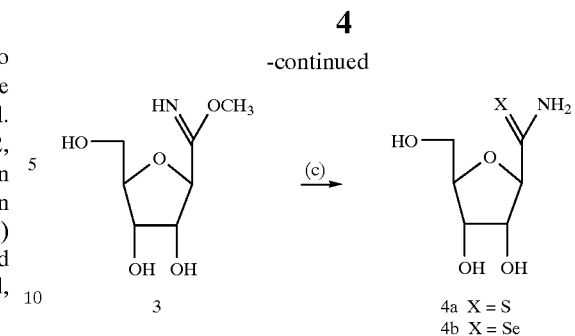

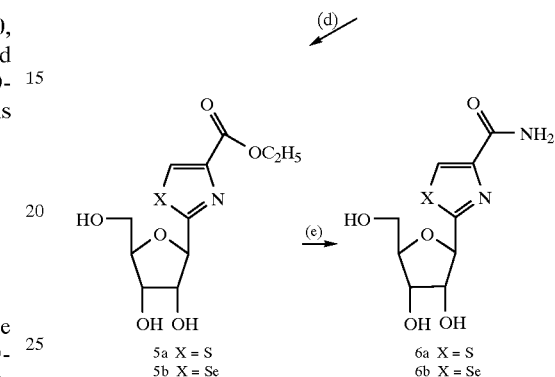

One difference in some of the embodiments, as compared to already published and protected procedures for obtaining ribo-C-nucleosides, is that in step (b) of the invention, deblocking of cyano sugar (i.e. the methanolysis of benzoyl ester) precede the introduction of sulfur or selenium—the synthesis of thio- or selenoamide and condensation of thia- or selenazolic ring. The deblocked cyano sugar is

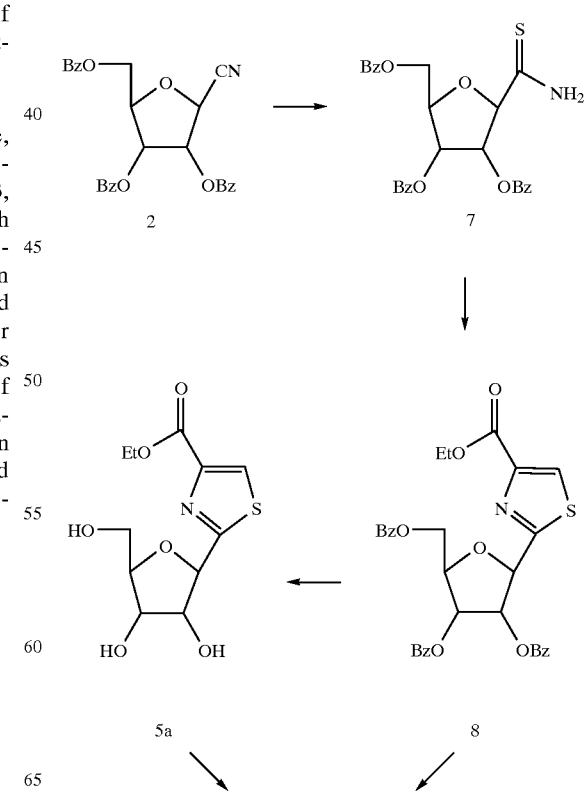

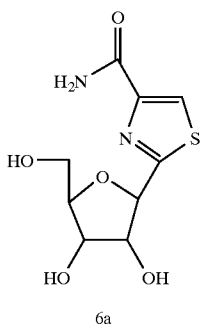

6a considerably more reactive, so that the duration of the reaction of thio- or selenoamide, thia- or selenazole and tiazofurin or selenazofurin formation is considerably decreased. All this contributes to a significantly improved yield, as compared to all syntheses published so far, by 46% and 55%, respectively.

Apart from this, some of the advantages reflected in the procedures of the invention are set out as follows:

a) The synthesis of 2,3-anhydro-3,4,6-tri-O-benzoyl-β-D-allononitrile 2 was improved by reducing the necessary quantities of trimethylsilyl cyanide and stannic(IV) chloride to between 1.3 and 1.6 mol and between 0.3 and 0.6 mol respectively, as compared to 1-O-acetyl-2,3,5-tri-O-benzoyl-β-D-ribofuranose, as well as by maintaining the temperature for the reaction between −5° and 0° C., which provided a substantially reduced formation of side-products and therefore an easier isolation. The reaction is interrupted by sodium hydroxide, instead of by sodium bicarbonate, while as a drying method—azeotropic distillation is used instead of magnesium sulfate.

b) Methanolysis of benzoyl ester results in formation of the reactive methyl-2,5-anhydro-D-allonimidate 3 at 35° to 45° C., with a very high yield of 91%, without using chromatographic purification, while utilizing methylene chloride for removing the produced methylbenzoate, with crystallization of product 3 occurring.

c) In the method of obtaining tiazofurin, thioamide 4a is obtained by the action of 1.2–1.4 mol of gaseous hydrogen sulfide in ethanol, in the presence of triethylamine, on imino-ester 3, wherein maintaining the temperature is of great importance. Hydrogen sulfide is introduced at −5° to 2° C. and at this temperature the reaction is carried out. The reaction is carried out at room temperature for additional 1 to 2 hours.

d) Thiazolic ring is formed in the reaction of thioamide and ethyl-α-bromopyruvate within 10 to 14 hours at room temperature in tetrahydrofuran, and in view of the fact that methanolysis of benzoyl groups has already been completed, no undesired α-anomer is produced, and therefore Dowex (Na+), which was used to prevent the formation α-anomer, is no longer required.

e) In the other method included by the procedure of the invention, namely obtaining of selenazofurin, the novelty reflects also in the method of synthesis of ethyl 2-β-D-ribofuranosylselenazole-4carboxylate 5b from methyl imidate 3, which comprises the introduction of a specified quantity of hydrogen selenide into ethanol cooled to 20° C., followed by addition of methyl imidate 3 in equimolar proportion. The reaction is carried out at 0° C. to 5° C., for 30 to 60 minutes, where the formed selenoamide 4b is not isolated, but ethyl-α-bromopyruvate is added immediately, in proportion of 1 to 1.5, which reacts immediately, producing solely ethyl 2-β-D-ribofuranosylselenazole-4-carboxylate 5b. In this way the yield has been considerably increased in this step.

f) Duration of the reaction of tiazofurin 6a formation was reduced from 72 hours to 48 hours. The reaction was carried out at 4° to 8° C., while crystallization from the mixture of 2-propanol and ethanol and recrystallization from ethanol give a satisfactory final product, with no use of chromatography or HPLC purification method.

Obtaining of selenazofurin 6b is carried out by the method known in the literature (W. J. Hennen et al., J.Org.Chem.1985, 50, 1741) in methanol solution of ammonia at room temperature.

In other embodiment, an important difference comprises the elimination of $Hg(CN)_2$ and $H_2S$ as reagent.

The invention will be further described by the following examples, which are in no way restrictive.

EXAMPLE 1

Obtaining of 2-β-D-ribofuranosylthiazole-4-carboxamide—compound 6a

Step (a): Obtaining of 2,3-Anhydro-3,4,6-tri-O-benzoyl-β-D-allononitrile—compound 2

1-O-acetyl-2,3,5-tri-O-benzoyl-β-D-ribofuranose 1, (100 g, 0.198 mol) was dissolved, with stirring, in methylene chloride (200 ml) and the mixture was cooled to 0°–2° C. Stannic(IV)chloride (12 ml, 0.102 mol) was added to the mixture and slowly, drop by drop, trimethylsilyl cyanide (40 ml, 0.300 mol), so that the temperature was maintained between 0° and 2° C. and the resulting mixture was stirred for further 90 minutes, at the temperature of −5 to 0° C. The reaction mixture was added slowly, while vigorously stirring, into cold (0° to 5° C.) 10% sodium hydroxide solution (360 ml), while maintaining the temperature between 5° and 8° C.

The layers were separated and the methylene chloride layer washed with water and evaporated to remove water to less than 0.1%, while the obtained syrup was recrystallized from absolute ethanol. The crystals were separated by filtration, washed with cold absolute ethanol and dried at 45° C. 70.4 g, 0.149 mol. 75.69% of the compound 2 was obtained, mp 74°–76° C., with the total yield of the compound 2 of 72.85 g (78.33%).

Step (b): Obtaining of Methyl-2,5-anhydro-D-allonimidate—compound 3

Sodium methoxide (1 g) was added into the mixture of 2,3-anhydro-3,4,6-tri-O-benzoyl-β-D-allononitrile 2 (70 g, 0.149 mol), obtained in the previous step, and methanol (460 ml, water less than 0.2%). The mixture was stirred at 40° C., under nitrogen atmosphere, for three hours, cooled to room temperature and neutralized with Dowex 50 W×8(H+) (30.9 g). Methanol solution was evaporated until turbidity was shown. The semi-solid residue was obtained, which was mixed with methylene chloride (130 ml), with crystallization of compound 3 occurring as a result. The crystals were separated by filtration, washed with methylene chloride and dried. 25.9 g (0.135 mol) of compound 3 was obtained, which was 91%, mp 134°–135° C.

Step (c): Obtaining of 2.5-Anhydro-D-allonthioamide—compound 4a

The mixture of previously obtained methyl-2,5-anhydro-D-allonimidate 3 (154.5 g, 0.804 mol) and absolute ethanol (1.35 l) was vigorously stirred and triethylamine (80.6 ml) was added. The mixture was cooled to 0° C. and, while maintaining the internal temperature, hydrogen sulfide was introduced into the mixture until a weight gain of 36.8 g (1.08 mol) had been achieved. The reaction mixture was stirred for 1 hour more, when the product 4 was formed as a whitish precipitate. Excess hydrogen sulfide was removed by purging out the mixture with nitrogen, with further precipitation of the product. The precipitate was separated by filtration, washed with ethyl acetate and dried at 45° to 50° C. (over KOH). 123.4 g (0.639 mol i.e. 79.5%), mp 154°–155° C. was obtained. The filtrate was partly evaporated and additional 25.9 g (0.134 mol) of compound 4 obtained, mp 158°–160° C.

The two crops were identical on thin-layer chromatography, so that they were combined. The total yield of compound 4 was 149.3 g, 0.773 mol, i.e. 96%.

Step (d): Obtaining of ethyl-2-β-D-ribofuranosylthiazole-4-carboxylate—compound 5a The mixture of methyl-2,5-anhydro-D-allonthioamide 4 (100 g, 0.518 mol) obtained in the previous step, tetrahydrofuran (1 l) and anhydrous magnesium sulfate (500 g) was stirred at room temperature for 1 hour in a nitrogen atmosphere. Ethyl-α-bromopyruvate (102 g, 0.523 mol) was added and the mixture vigorously stirred at room temperature for 12 hours. Triethylamine (75 ml, 0.538 mol) was then added and the mixture stirred for 1 hour more and then filtered. The filter cake was washed with tetrahydrofuran and the washes combined with the filtrate. The combined mixture was then evaporated. 170 g of red oil was obtained, which was chromatographed on silica gel column, packed in ethyl acetate and developed with ethyl acetate. 95.1 g of the compound 5 was obtained, mp 77–79° C. The filtrate and the washes were combined, evaporated under reduced pressure and the residue was triturated with ethyl acetate. The precipitate was separated by filtration, washed with ethyl acetate and dried. Additional 25.9 g of compound 5 was obtained, mp 75°–77° C. The total yield was 121 g, (0.418 mol) of the compound 5, i.e. 81%.

Step (e): Obtaining of the final product—compound 6

Methanol (620 ml), cooled to 0° C., was saturated with ammonia and cooled to −20° C. Ethyl 2-β-D-ribofuranosylthiazole-4-carboxylate (123.3 g, 0.43 mol), obtained in the previous step, was added to this solution. The mixture was stored at 5° C. for two days. The mixture was evaporated to obtain a sticky foam. The residue was dissolved in hot ethanol and than, while stirring, 2-propanol was added. 103.2 g of compound 6, mp 142°–144° C. were obtained and later an additional 3 g of compound 6, mp. 139°–140° C.

The two crops of solid were combined (106.2 g, 0.4 mol) and dissolved in boiling ethanol. The mixture was refrigerated (5° C.) for 2 hours and then filtered. The precipitate was washed with ethanol and dried. 89.3 g (0.34 mol) of the compound 6 was obtained, mp 144°–146° C., i.e. 80.5%.

The filtrate was evaporated to turbidity and the mixture vigorously stirred and cooled. The solid was collected by filtration, washed with ethanol and dried. 4.5 g (0.017 mol) of compound 6 was obtained, mp 142°–144° C., i.e. 4.1%. The total yield of tiazofurin 6 was 93.4 g (0.357 mol) i.e. 84.6%.

EXAMPLE 2

Obtaining of 2-β-D-ribofuranosylselenazole-4-carboxamide, compound 6b

Methyl-2,5-anhydro-D-allonimidate, compound 3, obtained as in the Example 1, is further treated with gaseous hydrogen selenide Step (c,d): Obtaining of ethyl 2-β-D-ribofuranosylselenazole-4-carboxylate, compound 5b Absolute ethanol (500 ml) was cooled at −20° C. and hydrogen selenide (16.6 g, 0.205 mol) was introduced. Into the prepared mixture, methyl-2,5-anhydro-D-allonimidate 3 (38.2 g, 0.2 mol) was added, after which the temperature was raised to 0° C. and at that temperature the reaction mixture was stirred for 45 minutes until the reaction of the starting compound 3 was completed. The mixture of redistilled ethyl-α-bromopyruvate (58.5 g, 0.3 mol) and ethanol (200 ml) were added in one portion. The red precipitate was formed instantly. The mixture was stirred for 30 minutes, then neutralized with sodium bicarbonate to pH 7 and filtered through a bed of celite. The filtrate was evaporated to obtain an oily residue which was purified chromatographically. The total yield of compound 5b was 47.7 g m.p. 96°–98° C., i.e. 71%.

Step (e): Obtaining of the final product, Compound 6b

The solution of ethyl 2-β-D-ribofuranosylselenazole-4-carboxylate 5b (23.5 g, 0.07 mol) obtained in the previous step, in methanol (300 ml) cooled to 0° C., saturated with ammonia and allowed to stand at room temperature for 24 h. The completion of ammonolysis was detected by thin layer chromatography, and after that the solution was evaporated to dryness and the residue was recrystallized from 2-propanol. The yield of compound 6b was 20.5 g, m.p. 129°–130° C., i.e. 85%.

EXAMPLE 3

2,5-Anhydro-3,4,6-tri-O-benzoyl-D-allonthioamide (7)

To a mixture of 2,3,5-tri-O-benzoyl-β-D-ribofuranosyl cyanide (4.71 g, 10 mmole) and diphenylphosphinothioic acid (2.99 g, 11.96 mmole) was added 2-propanol (70 ml) and water (35 ml). The reaction mixture was heated at 80–85° C. for 8 hours and evaporated to dryness. The residue was dissolved in ethyl acetate (150 ml), washed with 0.5N NaOH solution (1×100 ml), sat. NaHCO3 solution (1×100 ml), water (100 ml) and brine (100 ml). The organic extract was dried over anhydrous NaSO4, filtered and evaporated to dryness. The residue was dissolved in dimethyl sulfoxide (40 ml) and washed with ethyl ether:hexane (70:30; 2×50 ml) mixture. The DMSO extract was diluted with ethyl acetate (150 ml) and washed with water (2×100 ml) and brine (100 ml), dried over anhydrous NaSO4, filtered and concentrated to dryness. The residue was dissolved in minimum amount of hot ethanol cooled to room temperature and seeded with few crystals of pure thioamide. The titled compound crystalized out from ethanol after overnight standing. Yield: 5.2 g (99%), mp: 131–133° C. $^1$H NMR (CDCl$_3$); d 4.72 (m, 3H), 5.12 (m, 1H), 5.66 (m, 1H), 5.94 (t, 1H), 7.26–8.80 (m, 17H, 3XPh and NH$_2$). In place of diphenylphosphinothioic acid one could use O,O-dialkyl dithiophosphoric acids, thioacetamide, alkali-metal hydrogen sulfide, ammonium sulfide, water-soluble sulfides and polysulfides including P$_2$S$_5$.

EXAMPLE 4:

Ethyl 2-(2',3',5'-Tri-O-benzoyl-β-D-ribofuranosyl) thiazole-4-carboxylate(8)

Method A

To a stirred mixture of 2,5-anhydro-3,4,6-tri-O-benzoyl-D-allonthioamide (7, 1.28 g; 2.52 mmol) and Dowex 50W-X8, Na$^+$cation exchange resin (10 g) in EtOH (20 ml) was added ethyl bromopyruvate (0.98 g, 5.00 mmol) in one portion. The resulting mixture was stirred at 40° C. for 16 h, the resin was filtered and washed with EtOH (10 ml). The combined filtrate and washing were concentrated in vacuo to give the crude product as 1.4 g as brown syrup. For analytical purposes a small amount was purified by flash chromatography using methylene chloride:ethyl acetate (95:5) as the eluent. The crude material is suitable for further transformation.

Method B

To a stirred mixture of 2,5-anhydro-3,4,6-tri-O-benzoyl-D-allonthioamide (7, 1.27 g; 2.51 mmol) and dry MgSO4 (10 g) in dry THF (20ml) was added ethyl bromopyruvate (0.98 g, 5.00 mmol) in one portion. The resulting mixture was stirred at room temperature under argon atmosphere for 12 h. Triethyl amine (0.51 g, 5 mmol) was added, stirred for additional 1 h, the reaction was filtered and washed with THF (20 ml). The combined filtrate and washing were concentrated in vacuo to give the crude product as 1.4 g as brown syrup. The crude material was combined with the product from method A and used as such for the next reaction. $^1$H NMR (CDCl$_3$): d 1.35 (t, 3H), 4.38 (q, 2H), 4.60 (m, 1H), 4.72 (m, 1H), 4.84 (m,1H), 5.74 (m,1H), 5.85 (m, 2H), 7.26–7.60 (m, 9H, Ph), 7.86–8.14 (m, 6H, Ph), and 8.17 (s, 1H).

EXAMPLE 5

Ethyl 2-β-D-ribofuranosylthiazole-4-carboxylate (5a)

To a stirred solution of ethyl 2-(2',3',5'-tri-O-benzoyl-β-D-ribofuranosyl)thiazole-4-carboxylate 8 (3.01 g, 5.00 mmol) in dry ethanol (50 ml) under argon atmosphere was added NaOEt (1.02 g, 15 mmol) powder. The reaction mixture was stirred at room temperature overnight, neutralized with Dowex 50W-X8 H+ resin and filtere. The resin was washed with ethanol (20 ml) and the filtrate evaporated to dryness. The residue was dissolved in salt free water (50 ml) and washed with CHCl$_3$ (2×50 ml). The water extract was evaporated to dryness under reduced pressure to an oil. The oil was dissolved in minimum amount of warm ethyl acetate (10 mL). The solution was seeded with authentic 5 and once crystallization had begun the mixture was refrigerated (5° C.) for 16 h. The solid was collected by filtration, washed with cold (5° C.) ethyl acetate (5 mL), and dried (40° C., 1 mm); 1.2 g (83%), mp 74–78° C. $^1$H NMR (DMSO-d$_6$): d 1.31 (t, 3H), 3.46–3.64 (m, 2H), 3.8–4.12 (m, 3H), 4.30 (q, 2H), 4.84 (t, 1H) 4.94 (d, 1H), 5.04 (d, 1H), 5.4 (d,1H) and 8.49 (s,1H).

EXAMPLE 6

2-β-D-Ribofuranosylthiazole-4-carboxamide (Tiazofurin) (6a)

Method A

Ethyl 2-β-D-ribofuranosylthiazole-4-carboxylate (5a, 1.2 g, 4.15 mmol) was mixed with cold (−20° C.) methanolic ammonia (saturated at 0° C., 30 ml) and placed in a steel bomb. The flask was sealed and stirred at 5° C. for 2 days. The mixture was evaporated to a sticky foam. The residue was dissolved in hot ethanol (5 ml) and then, with stirring, 2-propanol (5 ml) was added. The mixture was allowed to stand at ambient temperature for 2 h and then was refrigerated (5° C.) for 1 d. The yellow solid was collected by filtration, washed with 2-propanol (5 m) and dried (25° C., 20 mm); 0.85 g (79%), mp 139–142° C. NMR (DMSO-d$_6$): d 3.59 (m, 2), 3.89 (s, 2), 4.07 (t, 1) 4.85 (t, 1), 4.93 (d, 1), 5.06 (d, 1), 5.36 (d, 1), 7.55 (s, 1), 7.70 (s, 1) and 8.21 (s, 1).

Method B

Ethyl 2-(2',3',5'-Tri-O-benzoyl-β-D-ribofuranosyl) thiazole-4-carboxylate (8, 3.01 g, 5.00 mmol) was mixed with cold (−20° C.) methanolic ammonia (saturated at 0° C., 50 ml) and placed in a steel bomb. The flask was sealed and stirred at 5° C. for 2 days. The mixture was evaporated to dryness to give a residue. The residue was partitioned between salt free water (50 ml) and CHCl$_3$ (50 ml) and extracted in water. The water extract was washed with CHCl$_3$ (50 ml) again and evaporated to dryness under reduced pressure. The residue that obtained was dissolved in hot absolute ethanol (10 ml) which on standing the pure product crystallized as colourless material. Yield 1.1 g (85%); mp 139–142° C.

EXAMPLE 7

2,3,5-Tri-O-benzoyl-β-D-ribofuranosyl-1-carbonitrile (2)

A mixture of 1-O-acetyl-2,3,5-tri-O-benzoyl-β-D-ribofuranose (1, dried at 60° C., 1 mm, 12 h) (630 g, 1.249 mol), trimethylsilyl cyanide (dried over molecular sieves, 24 h) (250 mL, 1.875 mol), and dichloromethane (dried over magnesium sulfate and stored over molecular sieves) (1.25 L) was stirred and cooled to 0–2° C. Stannic chloride (50 mL, 0.425 mol) was added slowly (1.5 h) while maintaining a reaction temperature of 0–2° C. and resulting mixture was stirred and maintained at −5 to 0° C. for an additional 1.5 h. The reaction mixture was added slowly (30 min) and vigorous stirring to a cold (5° C.) 10% sodium hydroxide solution (1.5 L) which was maintained at 5–8° C. throughout the addition. The layers were separated and the organic layer was washed with water (3×500 mL) until neutral and then dried over anhyd. magnesium sulfate (approx. 150 g). The mixture was filtered and the drying agent was washed with dichloromethane (3×500 mL). The filtrate and washings were combined and the solution was concentrated (<30° C., 20 mm) to a volume of 2–2.5 L. The remaining solution was filtered through a bed (13.5 cm id×6.5 cm) of Silica Gel and the bed was further eluted with dichloromethane (2.5 L). The dichloromethane solutions were combined and evaporated (<30° C., 20 mm) to a syrup (approx. 750 mL). The syrup was mixed with ethanol (1.5 L) and the mixture was heated (approx. 60° C.) to obtain a homogeneous solution. Seed crystals of 2 were added and the solution was stirred at ambient temperature for 2 h and then slowly cooled to 0° C. over 2 h period. The crystalline solid was collected, washed with cold (−5° C.) ethanol (3×600 mL), washed with hexanes (600 mL), and dried at 45° C. and 1 mm for 12 h; 452 g (0.959 mol, 76%), mp 73–75° C. (lit mp 78–80° C.). $^1$H NMR (DMSO-d$_6$): δ4.61 (m, 2), 4.80 (q, 1), 5.49 (d, 1), 5.88 (t, 1), 6.05 (t, 1), 7.45–7.57 (m, 6), 7.64–7.71 (m, 4), 7.88–7.94 (m, 4) and 8.07 (d, 2).

EXAMPLE 8

Methyl 2,5-Anhydro-D-allonimidate (3)

Commercial sodium methoxide (anhydrous, freshly opened container) (6.5 g, 0.12 mol) was added to a vigorously stirred mixture of 2,3,5-tri-O-benzoyl-β-D-ribofuranosyl-1-carbonitrile (2) (470.8 g, 1.0 mol) and methanol (3.1 L). The resulting mixture was stirred at ambient temperature and under a nitrogen atmosphere for 24 h and then was neutralized by addition of Dowex 50W×8 (H$^+$) (208 g, washed well with water and then with methanol). The resin was removed by filtration and washed with methanol (3×500 mL). The filtrate and methanol washes were combined, charcoal (25 g) was added, and the mixture was stirred for 0.5 h. The charcoal was removed by filtration and washed with methanol (3×20 mL). The filtrate and the washes were combined and the methanol was removed by evaporation (30–35° C., 20 mm). The semisolid residue was stirred with a 5% methanol in dichloromethane solution (500 mL) and the mixture was stored at 10° C. for 2 d. The solid was collected by filtration, washed with dichloromethane (3×350 mL) and dried (50–55° C., 20 mm) over $P_2O_5$ for 2 d; 158 g (0.826 mol, 82%), mp 133–134 ° C. dec. $^1$H NMR (DMSO-$d_6$): δ3.2–3.9 (m, 5), 3.66 (s, 3), 4.07 (d, 1), 5.0 (br s, 3), and 8.31 (s, 1).

EXAMPLE 9

2,5-Anhydro-D-allonthioamide (4a)

A mixture of methyl 2,5-anhydro-D-allonimidate (3) (154.5 g, 0.804 mol) and ethanol (1.35 L) was vigorously stirred and triethylamine (80.6 mL) was added. The mixture was cooled to 0° C. and, while maintaining an internal temperature of −3 to 0° C., hydrogen sulfide was bubbled into the solution until a weight gain of 36.8 g had been achieved. The reaction was stirred in the cold (0° C.) for 1 h more and then the cooling bath was removed. After the additional 1 h excess hydrogen sulfide was removed by purging the reaction mixture with nitrogen. Ethyl acetate (500 mL) was added and the mixture was stored at 5° C. for 16 h. The solid was collected by filtration, washed with ethyl acetate (3×90 mL), and dried (45–50° C., 20 mm) over potassium hydroxide for 12 h; 123.4 g (0.639 mol, 79.5%), mp 153–154° C. The filtrate was evaporated (40° C., 20 mm) and the residue was triturated with a ethyl acetate:ethanol, 3:1, mixture (50 mL) to obtain more solid. The solid was collected by filtration, washed with ethyl acetate (25 mL), and dried as above; 25.9 g (0.134 mol, 16.5%), mp 158–160° C. The two crops identical on TLC and were combined; 139.3 g (0.773 mol, 96%). $^1$H NMR (DMSO-$d_6$): δ3.5–3.9 (m, 4), 4.05 (m, 1), 4.38 (d, 1), 4.85–5.35 (m, 3) and 9.35–9.95 (2 br s, 2).

EXAMPLE 10

Ethyl 2-β-D-Ribofuranosylthiazole-4-carboxylate (5a)

A mixture of methyl 2,5-anhydro-D-allonthioamide (4) (100 g, 0.518 mol), tetrahydrofuran (1 L), and anhyd. magnesium sulfate (500 g) was protected from moisture and stirred at ambient temperature for 6 h. Ethyl bromopyruvate (102 g, 0.523 mol) was added and mixture was vigorously stirred at ambient temperature for 1 d. Triethylamine (75 mL, 0.538 mol) was added and the mixture was stirred for 1 h more then filtered. The filter cake was washed with tetrahydrofuran (6×250 mL) and the washes were combined with reaction filtrate. The tetrahydrofuran solution was evaporated (35° C., 20 mm) to obtain a red oil; 156.5 g. The filter from the reaction mixture was suspended in dichloromethane (1 L) and the mixture was stirred for 0.5 h. The mixture was filtered and filter cake was washed with dichloromethane (250 mL), combining the wash with the filtrate. The filter cake was further extracted, by suspension and refiltration, with a methanol:dichloromethane, 1:9, mixture (2×1 L). All of the extracts and washes were combined and evaporated (35° C., 20 mm) to obtain a semisolid residue. The residue was extracted with tetrahydrofuran (5×100 mL) while removing the solid by filtration. The extracts were combined and evaporated to give additional red oil; 18.3 g. The two crops of oil were combined (174.8 g) and dissolved in a mixture of ethyl acetate (500 mL) and tetrahydrofuran (200 mL). The solution was applied to a column (13 cm i.d.) of silica gel (1 kg, slurried in ethyl acetate). The column was flash eluted with ethyl acetate (5 L) and then flash eluted with a methanol:ethyl acetate, 1:19, mixture (7 L). The eluate was collected in 500 mL fractions and the fractions containing predominately 5 were combined and those fractions containing a mixture of 5 and byproduct were combined separately.

The solution containing predominately 5 was concentrated (40° C., 20 mm) to a volume of approx. 600 mL and the solid which had separated was removed by filtration, washed with ethyl acetate (3×100 mL), and dried (40° C., 1 mm); 75.7 g mp 75–79° C. The combined filtrate and washes was evaporated (40° C., 20 mm) to dryness. The residue was stirred with ethyl acetate (100 mL) and the solid was collected by filtration, washed with ethyl acetate (3×50 mL), and dried (40° C., 1 mm); 13.2 g, 76–79° C. The combined filtrate and washes was evaporated (40° C., 20 mm) to dryness. The residue was stirred with ethyl acetate (50 mL) and the mixture was refrigerated (5° C.) for 16 h. The solid was collected by filtration, washed with ethyl acetate (4×25 mL) and dried (40° C., 1 mm); 6.2 g, mp 75–79° C. The filtrate and washes were combined and reserved for later processing.

The solution containing a mixture of 5 and a byproduct was evaporated (40° C., 20 mm) to obtain a red oil (40 g). The oil was dissolved in warm (40° C.) ethyl acetate (100 mL). The solution was seeded with authentic 5 and once crystallization had begun the mixture was refrigerated (5° C.) for 16 h. The solid was collected by filtration, washed with cold (5° C.) ethyl acetate (3×50 mL), and dried (40° C., 1 mm); 23.2 g, mp 59–67° C. The combined filtrate and washes was reserved for later processing.

The two ethyl acetate solutions from above were combined and evaporated (40° C., 20 mm) to obtain a red oil. The oil was dissolved in ethyl acetate (150 mL) and the solution was applied to a column (7 cm i.d.) of silica gel (300 g, slurried in ethyl acetate). The column was flash eluted with ethyl acetate (1.5 L), then flash eluted with a methanol:ethyl acetate, 1:19, mixture (1 L), and finally flash eluted with a 1:9 methanol:ethyl acetate mixture (2 L). Fractions of 250 mL were collected and fractions containing 5 were pooled and evaporated (40° C., 20 mm). The residual oil was coevaporated with ethyl acetate (3×50 mL) and then dissolved in hot ethyl acetate (50 mL). The solution was seeded with 5 and allowed to stand at ambient temperature for 6 h. The solid which had separated was collected by filtration, washed with ethyl acetate (2×50 mL), and dried (40° C., 1 mm); 3.0 g, mp 75–77° C.

The five crops of 5 were combined to give a yield of 121.3 g (0.419 mol, 81%). $^1$H NMR (DMSO-d6): δ1.31 (t, 3), 3.46–3.64 (m, 2), 3.8–4.12 (m, 3), 4.30 (q, 2) 4.84 (t, 1), 4.94 (d, 1), 5.04 (d, 1), 5.4 (d, 1) and 8.49 (s, 1).

EXAMPLE 11

2-β-D-Ribofuranosylthiazole-4-carboxamide (Tiazofurin) (6)

Ethyl 2-β-D-ribofuranosylthiazole-4-carboxylate (5, 120.8 g, 0.418 mol) was mixed with cold (−20° C.) methanolic ammonia (saturated at 0° C.). The mixture was protected from moisture and at 5° C. for 2 days. The mixture was evaporated (40° C., 20 mm) to a sticky foam. The residue was dissolved in hot ethanol (500 mL) and then, with stirring, 2-propanol (500 mL) was added. The mixture was allowed to stand at ambient temperature for 2 h and then was refrigerated (5° C.) for 1 d. The yellow solid was collected by filtration, washed with 2-propanol (2×100 mL) and dried (25° C., 20 mm); 98.0 g, mp 139–142° C. The washes were combined with the filtrate and the solution was evaporated (40° C., 20 mm) to dryness. The residue was dissolved in hot ethanol (100 mL). The solution was allowed to stand at ambient temperature until crystallization began and then was stored at 5° C. for 1 d. The solid was collected by filtration, washed with ethanol (2×25 mL), and dried (25° C., 20 mm); 6.9 g, mp 138–139° C. The two crops of solid (104.9 g, 0.403 mol, 96%) were combined and dissolved in boiling ethanol (1.1 L). Norit A (10 g) was added and the mixture was stirred and boiled for 5 min. The mixture was filtered through an ertel pad and pad was washed with hot ethanol (3×100 ml). The washes were combined with the filtrate; the solution was stirred rapidly and cooled in ice bath for 1 h. The mixture was refrigerated (5° C.) for 3 d. The solid was collected by filtration, washed with ethanol (2×100 mL), and dried (50° C., 1 mm) for 1 d; 91.1 g (0.35 mol, 84%), mp 140–142° C. The combined filtrate and washes was concentrated to a volume of approx. 350 mL. The solution was heated to boiling and 2-propanol (200 mL) was added. The solution was concentrated to a volume of 300 mL and then refrigerated (5° C.) for 1 d. The solid was collected by filtration, washed with 2-propanol (3×25 mL), and dried (50° C., 1 mm); 9.4 g (0.036 mol, 8%), mp 138–139° C. The crops were not combined. $^1$H NMR (DMSO-d$_6$): δ3.59 (m, 2), 3.89 (s, 2), 4.07 (t, 1), 4.85 (t, 1), 4.93 (d, 1), 5.06 (d, 1), 5.36 (d, 1), 7.55 (s, 1), 7.70 (s, 1) and 8.21 (s, 1).

The foregoing written specification is considered to be sufficient to enable one skilled in the art to practice the invention. Indeed, various modifications of the above-described procedures for carrying out the invention which are apparent to those skilled in the field of organic chemistry or related fields are intended to be within the scope of the following claims.

What is claimed is:

1. A procedure for obtaining ribo-C-nucleoside of general formula 6a

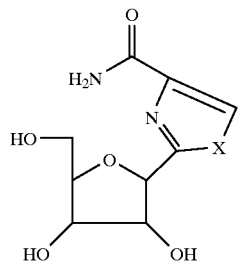

wherein X=S of Se, comprising the steps:

(A). providing a furanose (1);

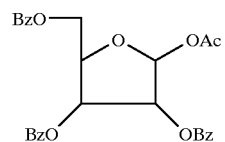

(B). introducing a cyano group in the furanose (1) at the 1' position in a single step to form the structure (2);

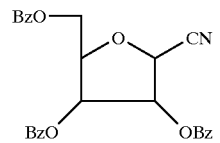

(C). converting the cyano group of (2) via indirect conversion (3,4) to thiocarboxyamide wherein $R_1$ is $CH_3$ or $CH_2CH_3$;

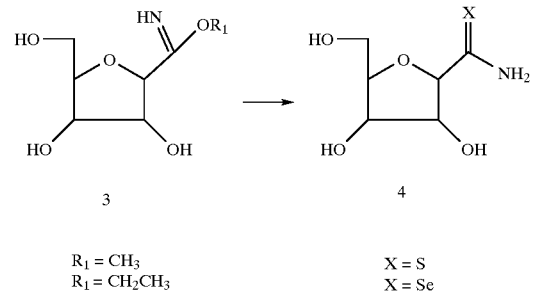

$R_1 = CH_3$
$R_1 = CH_2CH_3$ $X = S$
$X = Se$ (D). closing of the heterocyclic ring portion to form compound 9 wherein $R_2$ is $CH_3$ or Et; and

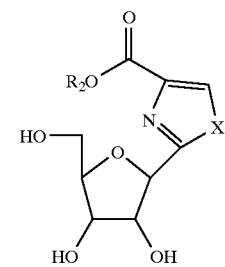

(E). converting $OR_2$ into $NH_2$.

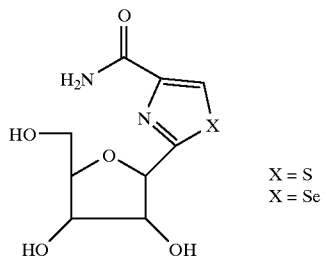

$X = S$
$X = Se$

2. The procedure of claim 1 wherein the hydroxyl groups of the furanose are blocked prior to step B and deblocking occurs prior to step D.

3. The procedure of claim 1 wherein the hydroxyl groups of the furanose are blocked prior to step B and deblocking occurs after step D.

4. The procedure of claim 1 wherein a reagent utilized in step B comprises alkylsilylcyanide.

5. The procedure of claim 1 wherein a reagent utilized in direct conversion of the cyano group to HN=C—OR of step C comprises of NaOMe or NaOEt.

6. The procedure of claim 1 wherein a reagent utilized in direct conversion of the cyano group to thiocarboxyamide of step C comprises at least one of (a) diphenylphosphino thionic acid
(b) O,O-dialkyldithiophosphoric acids
(c) thioacetamide
(d) alkali-metal hydrogen sulfide
(e) ammonium sulfide
(f) water-soluble sulfides
(g) polysulfides
(h) $P_2S_5$.

7. The procedure of claim 1 wherein a reagent utilized in indirect conversion of the cyano group to thiocarboxyamide of step C comprises of $H_2S$.

8. The procedure of claim 1 wherein a reagent utilized in step D comprises at least one of (a) anhydrous $MgSO_4$; (b) Dowex $H^+$ ($Na^+$ form); (c) molecular sieves.

9. The procedure of claim 1 in which a reagent of step E includes ammonia in methanol, ethanol, DMF, THF and $CH_2Cl_2$.

10. A multi-step procedure for obtaining ribo-C-nucleoside of general formula 6

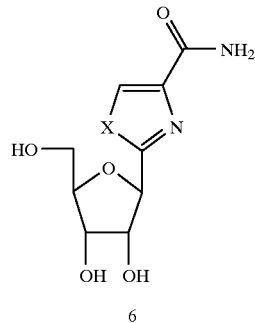

6 wherein X=S or Se wherein the synthesis is carried out in five steps, according to the following scheme:

Step (a)

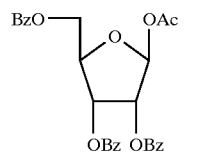 $\xrightarrow{(CH_3)_3SiCN}{SnCl_4}$ 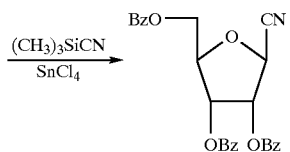

1-O-acetyl-2, 3, 5-tri-O-benzoyl-β-D-ribofuranose (compound 1)

2, 3-Anhydro-3, 4, 6-tri-O-benzoyl-β-D-allononitrile (compound 2)

Step (b)

Compound 2 $\xrightarrow{NaOCH_3}{CH_2Cl_2}$ 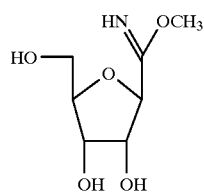

Methyl-2, 5-anhydro-D--allonomidate (compound 3)

Step (c)

Compound 3 $\xrightarrow{H_2X}{X = S, Se}$ 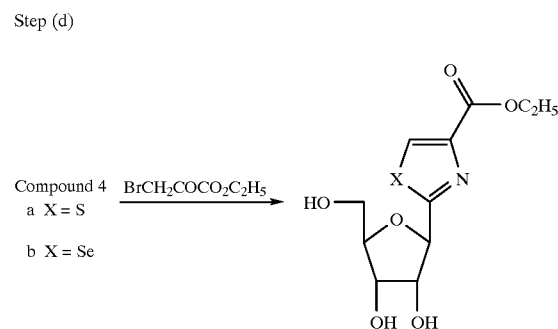

X = S   2, 5-Anhydro-D-allonthioamide (compound 4a)

X = Se  2, 5-Anhydro-D-allonselenoamide (compound 4b)

Step (d)

Compound 4
a X = S
b X = Se
$\xrightarrow{BrCH_2COCO_2C_2H_5}$ 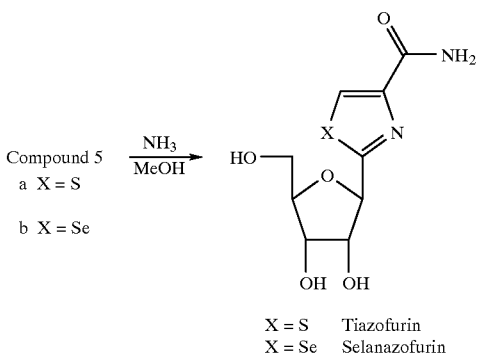

X = S   Ethyl-2-β-D-ribofuranosylthiazole-4-carboxylate (compound 5a)

X = Se  Ethyl-2-β-D-ribofuranosylselanazole-4-carboxylate (compound 5b)

Step (e)

Compound 5
a X = S
b X = Se
$\xrightarrow{NH_3}{MeOH}$ 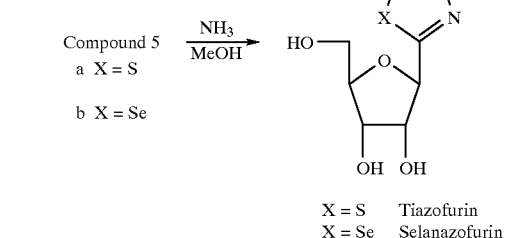

X = S   Tiazofurin
X = Se  Selanazofurin

11. A procedure for obtaining ribo-C-nucleoside of general formula 6a

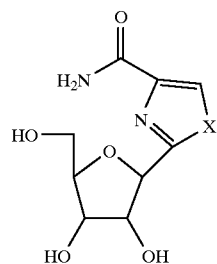

wherein X=S or Se, comprising the steps:

(A). providing a ribose;
(B). introducing a cyano group at 1 position using trimethylsilylcyanide;
(C). converting the cyano group directly to thiocarboxylamide using diphenylphosphinothionic acid;
(D). closure of the heterocyclic ring portion to form compound 10 using ethylbromopyruvate and MgSO4 or Dowex X8 H$^+$ resin Na$^+$ form, wherein $R_2$ is Et and R is benzoyl;

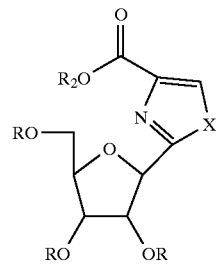

(E). converting $OR_2$ into $NH_2$ using ammonia in methanol.